United States Patent
Coyne et al.

(10) Patent No.: US 11,844,506 B2
(45) Date of Patent: Dec. 19, 2023

(54) DEVICES AND METHODS FOR CUTTING, ALIGNING, AND JOINING BONES

(71) Applicant: NEXTREMITY SOLUTIONS, INC., Warsaw, IN (US)

(72) Inventors: Matthew Coyne, Warsaw, IN (US); Ryan Schlotterback, Warsaw, IN (US); Adam Finley, Warsaw, IN (US); Bradley Boysen, Warsaw, IN (US)

(73) Assignee: MEDARTIS AG, Basel (CH)

( * ) Notice: Subject to any disclaimer, the term of this patent is extended or adjusted under 35 U.S.C. 154(b) by 79 days.

(21) Appl. No.: 17/655,874

(22) Filed: Mar. 22, 2022

(65) Prior Publication Data

US 2023/0301644 A1  Sep. 28, 2023

(51) Int. Cl.
  *A61B 17/02* (2006.01)
  *A61B 17/56* (2006.01)

(52) U.S. Cl.
  CPC ...... *A61B 17/025* (2013.01); *A61B 2017/565* (2013.01)

(58) Field of Classification Search
  CPC .................. A61B 17/025; A61B 2017/565
  See application file for complete search history.

(56) References Cited

U.S. PATENT DOCUMENTS

| 4,338,927 A | * | 7/1982 | Volkov | A61B 17/6425 606/56 |
| 5,042,983 A | | 8/1991 | Rayhack | |
| 6,030,391 A | * | 2/2000 | Brainard | A61B 17/15 606/82 |

(Continued)

FOREIGN PATENT DOCUMENTS

| EP | 1508316 A1 | 2/2005 |
| GB | 2583572 A | 11/2020 |

(Continued)

OTHER PUBLICATIONS

UKIPO Search Report dated Feb. 23, 2021.
UKIPO Search Report dated Sep. 20, 2021.
UKIPO Search Report dated Oct. 21, 2021.

*Primary Examiner* — Christian A Sevilla
(74) *Attorney, Agent, or Firm* — Heslin Rothenberg Farley & Mesiti P.C.; Victor A. Cardona, Esq.

(57) ABSTRACT

A bone displacement system includes a removable guide and frame. The removable guide includes a proximal anchoring portion and a distal anchoring portion. The proximal anchoring portion has a proximal anchoring aperture for receiving a first wire to connect the guide to a proximal bone. The distal anchoring portion has a distal anchoring aperture for receiving a second wire to connect the guide to a distal bone. The guide includes a slot configured to receive a tool. The frame includes a compression-distraction mechanism and a rotation mechanism. The compression-distraction mechanism is connected to the rotation mechanism and engageable with the proximal bone. The rotation mechanism includes a distal aperture for receiving the second wire to connect the rotation mechanism to the distal bone, and the compression-distraction mechanism is configured to move the rotation mechanism and the distal bone relative to the proximal bone. Further disclosed is a bone displacement method.

24 Claims, 15 Drawing Sheets

(56) References Cited

U.S. PATENT DOCUMENTS

| | | | |
|---|---|---|---|
| 2015/0182273 A1* | 7/2015 | Stemniski | A61B 90/39 |
| | | | 606/96 |
| 2016/0235414 A1 | 8/2016 | Hatch et al. | |
| 2017/0014143 A1* | 1/2017 | Dayton | A61B 17/8061 |
| 2017/0020537 A1 | 1/2017 | Tuten | |
| 2017/0079669 A1 | 3/2017 | Bays et al. | |
| 2018/0110530 A1 | 4/2018 | Wagner et al. | |
| 2019/0274745 A1 | 9/2019 | Smith et al. | |
| 2019/0357919 A1 | 11/2019 | Fallin et al. | |
| 2021/0077131 A1 | 3/2021 | Denham et al. | |
| 2022/0151644 A1* | 5/2022 | Cundiff | A61B 17/66 |

FOREIGN PATENT DOCUMENTS

| | | |
|---|---|---|
| GB | 2589960 A | 6/2021 |
| WO | 2019113394 A1 | 6/2019 |

* cited by examiner

DEVICES AND METHODS FOR CUTTING, ALIGNING, AND JOINING BONES

CROSS-REFERENCE TO RELATED APPLICATIONS

The present application is related to U.S. application Ser. No. 17/022,761 filed Sep. 16, 2020, which claims the benefit of U.S. Provisional Application Ser. No. 62/900,920 filed Sep. 16, 2019, U.S. Provisional Application No. 62/991,879 filed Mar. 19, 2020, U.S. application Ser. No. 17/238,920 filed Apr. 23, 2021, which claims the benefit of U.S. Provisional Application Ser. No. 63/015,052 filed Apr. 24, 2020, and U.S. application Ser. No. 17/652,195 filed Feb. 23, 2022; which are incorporated herein by reference in their entireties.

FIELD OF THE INVENTION

This application relates to apparatuses, devices, and methods for cutting, adjusting, and joining bones.

DESCRIPTION OF THE RELATED ART

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The bunion is a disease of the joint and soft tissue. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and, in some cases, very painful during walking and other weight bearing activities. Bunions may also be painful and debilitating condition that prevents wearing shoes. Genetics and poor shoe design are the causes. The angle between the metatarsal of the second digit is a means to quantify the degree of deformity.

Painful bunions are corrected by surgical soft tissue management and surgical bone reforming. The first metatarsal is corrected by sectioning it with a saw and moving the head laterally. There are numerous cut locations from the proximal to distal regions, namely the chevron, Ludloff, Mau and proximal. The bones are shifted, and held in place with screws, staples or plates. Sometimes adjacent joints are fused to stabilize the reconstruction.

A goal of a proximal osteotomy procedure is to surgically treat hallux valgus. An orthopedic foot and ankle surgeon realigns to a normal toe shape by placing the first metatarsal straight with the medial cuneiform bone. For example, a first metatarsal may be cut into sections and realigned. This will allow the first toe to stay straight and prevent the bunion from coming back.

Thus, a need exists for devices, systems, and methods for treating foot deformities that are repeatable yet adaptable to particular clinical situations.

SUMMARY OF THE INVENTION

The present invention provides, in a first aspect, a bone displacement system which includes a removable guide and a frame. The removable guide includes a proximal anchoring portion and a distal anchoring portion. The proximal anchoring portion has a proximal anchoring aperture for receiving a first wire to connect the guide to a proximal bone. The distal anchoring portion has a distal anchoring aperture for receiving a second wire to connect the guide to a distal bone. The guide further includes a slot configured to receive a tool. The frame includes a compression-distraction mechanism and a rotation mechanism. The compression-distraction mechanism is connected to the rotation mechanism and engageable with the proximal bone. The rotation mechanism includes a distal aperture for receiving the second wire to connect the rotation mechanism to the distal bone, and the compression-distraction mechanism is configured to move the rotation mechanism and the distal bone relative to the proximal bone.

The present invention provides, in a second aspect, a mechanism for bone displacement including a frame. The frame includes a compression-distraction mechanism and a rotation mechanism. The compression-distraction mechanism is connected to the rotation mechanism and engageable with a proximal bone. The rotation mechanism includes a distal aperture for receiving a wire to connect the rotation mechanism to a distal bone. The compression-distraction mechanism is configured to move the rotational mechanism and to move the proximal bone and distal bone relative to each other.

The present invention provides, in a third aspect, a method for bone displacement. The method includes inserting a first wire through a proximal anchoring portion of a removable guide into a proximal bone. The method further includes inserting a second wire through a distal anchoring portion of the guide into a distal bone. The method includes performing an osteotomy in a slot in the guide, then removing the guide. The method further includes inserting a frame comprising a compression-distraction mechanism and a rotation mechanism. The method further includes connecting the compression-distraction mechanism to the first wire. The method includes connecting the rotation mechanism to the second wire. The method further includes moving the rotation mechanism and/or the compression-distraction mechanism under conditions effective to adjust an alignment of axes of the proximal bone and the distal bone relative to each other.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Figure 1:
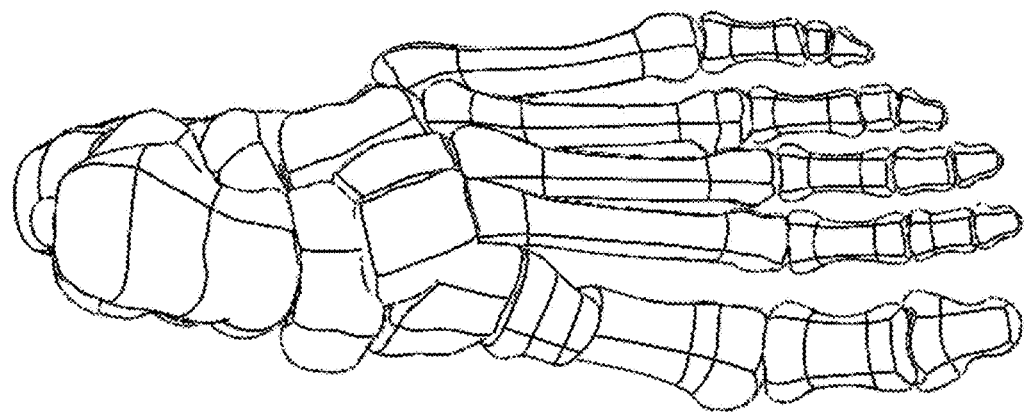
FIG. 1 is a depiction of bunions in a subject before (left) and after (right) a proximal osteotomy.
Figure 1:
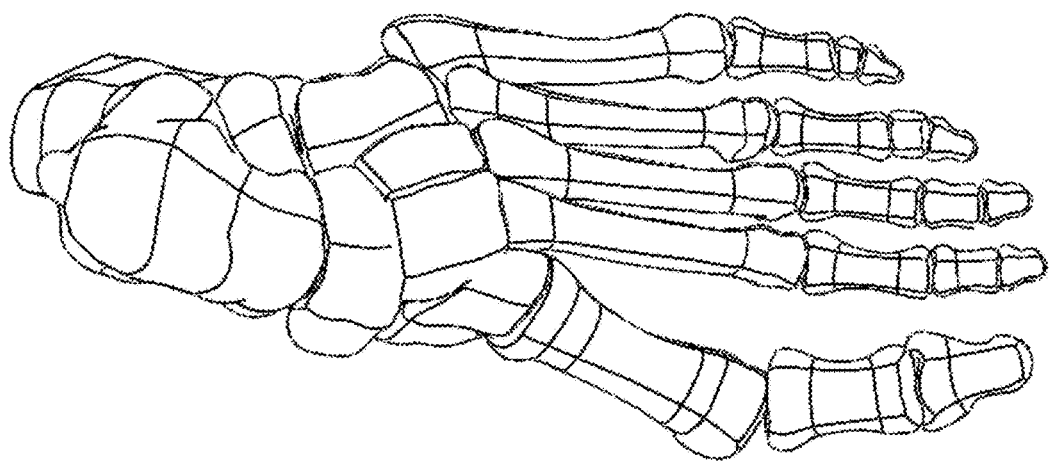
Figure 2:
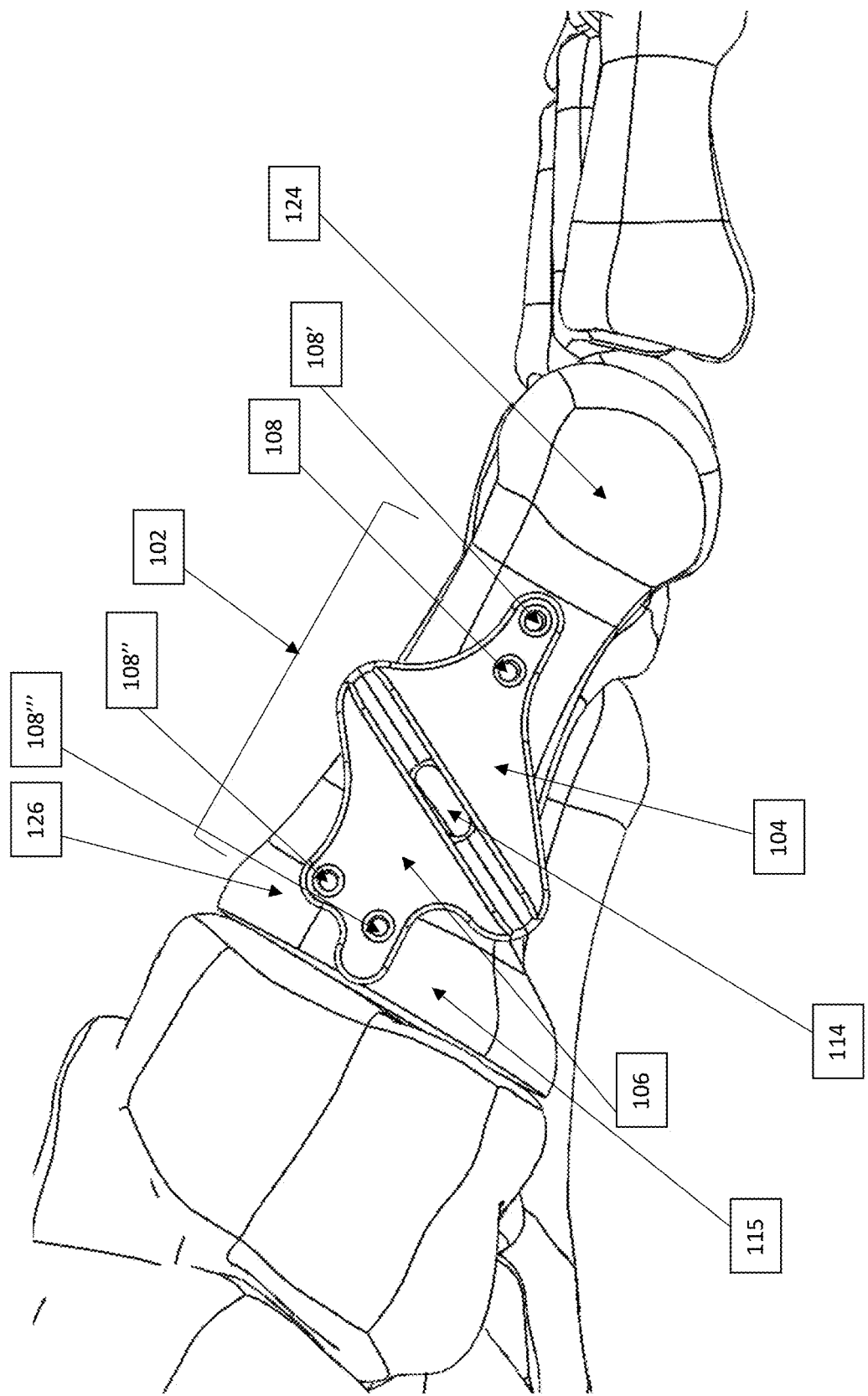
FIG. 2 is a perspective view of a removable guide on the medial aspect of a foot in accordance with the system described herein.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in, for example, FIG. 2.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As will be described below, the present invention includes systems and methods for correcting a deformity of the human foot. As depicted in FIGS. 2-12, a bone displacement system 10 may include a removable guide 102 and a frame 116. Removable guide 102 includes a proximal anchoring portion 106 and a distal anchoring portion 104. Proximal anchoring portion 106 has at least one proximal anchoring aperture 108" and/or 108'" for receiving at least one first wire 112 and/or 112' to connect guide 102 to a proximal bone portion or bone 126. Distal anchoring portion 104 has at least one distal anchoring aperture 108 and/or 108' for receiving at least one second wire 110 and/or 110' to connect guide 102 to a distal bone portion or bone 124. Guide 102 further includes a slot 114 configured to receive a tool 135 such as a burr or a saw. Frame 116 includes a compression-distraction mechanism 120 and a rotation mechanism 118. Compression-distraction mechanism 120 is connected to rotation mechanism 118 and engageable with proximal bone 126. Rotation mechanism 118 includes a distal aperture 123 for receiving at least one second wire 110 and/or 110' to connect rotation mechanism 118 to distal bone 124, and compression-distraction mechanism 120 is configured to move rotation mechanism 118 and distal bone 124 relative to proximal bone 126.

As further depicted in FIGS. 6-12, frame 116 may include, in rotation mechanism 118, a first trolley 30, and compression-distraction mechanism 120 may include a second trolley 31.

Figure 6:
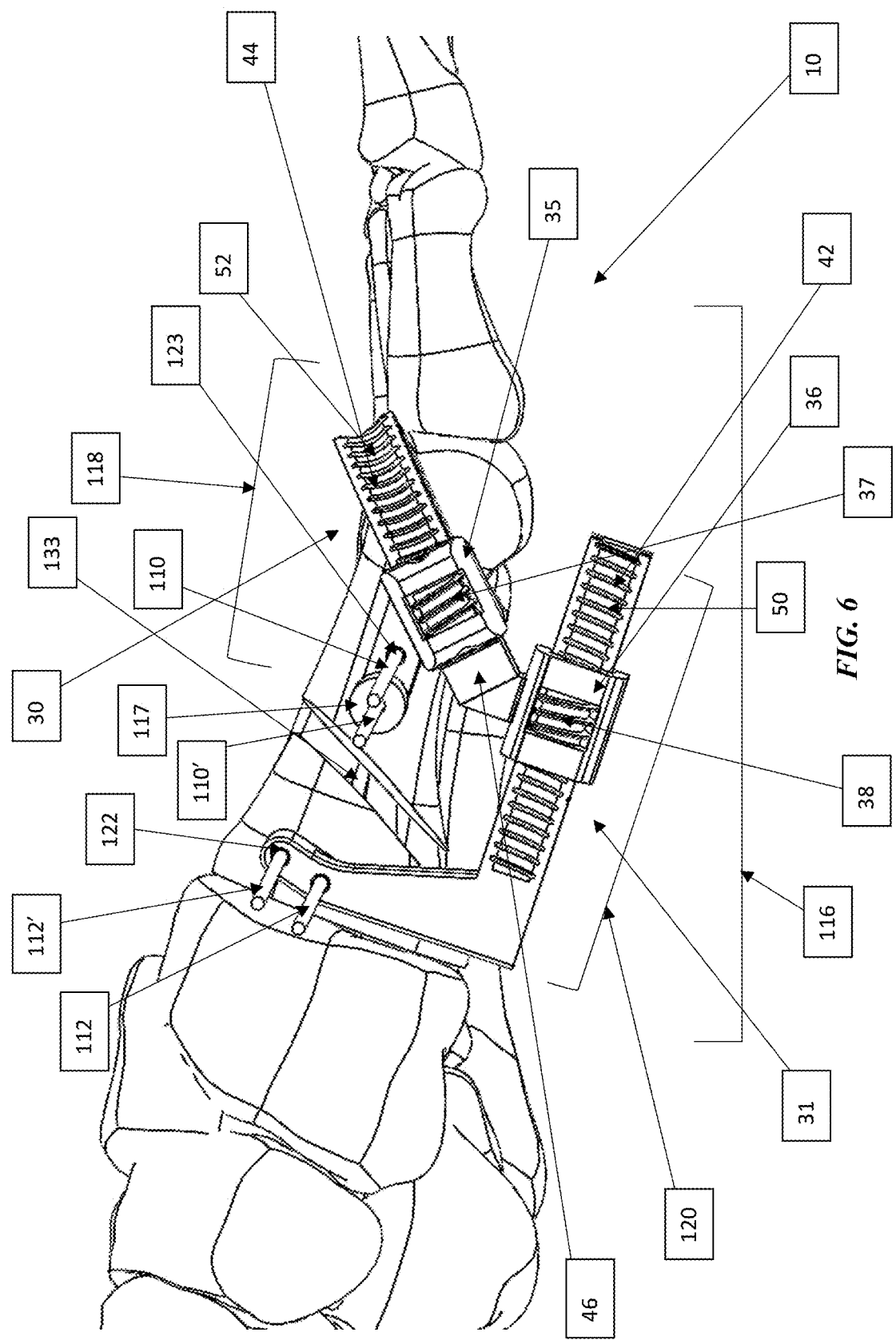
FIG. 6 is a perspective view of the frame and wires in accordance with the system described herein, where the guide is removed and the frame is inserted over the wires.
Figure 7:
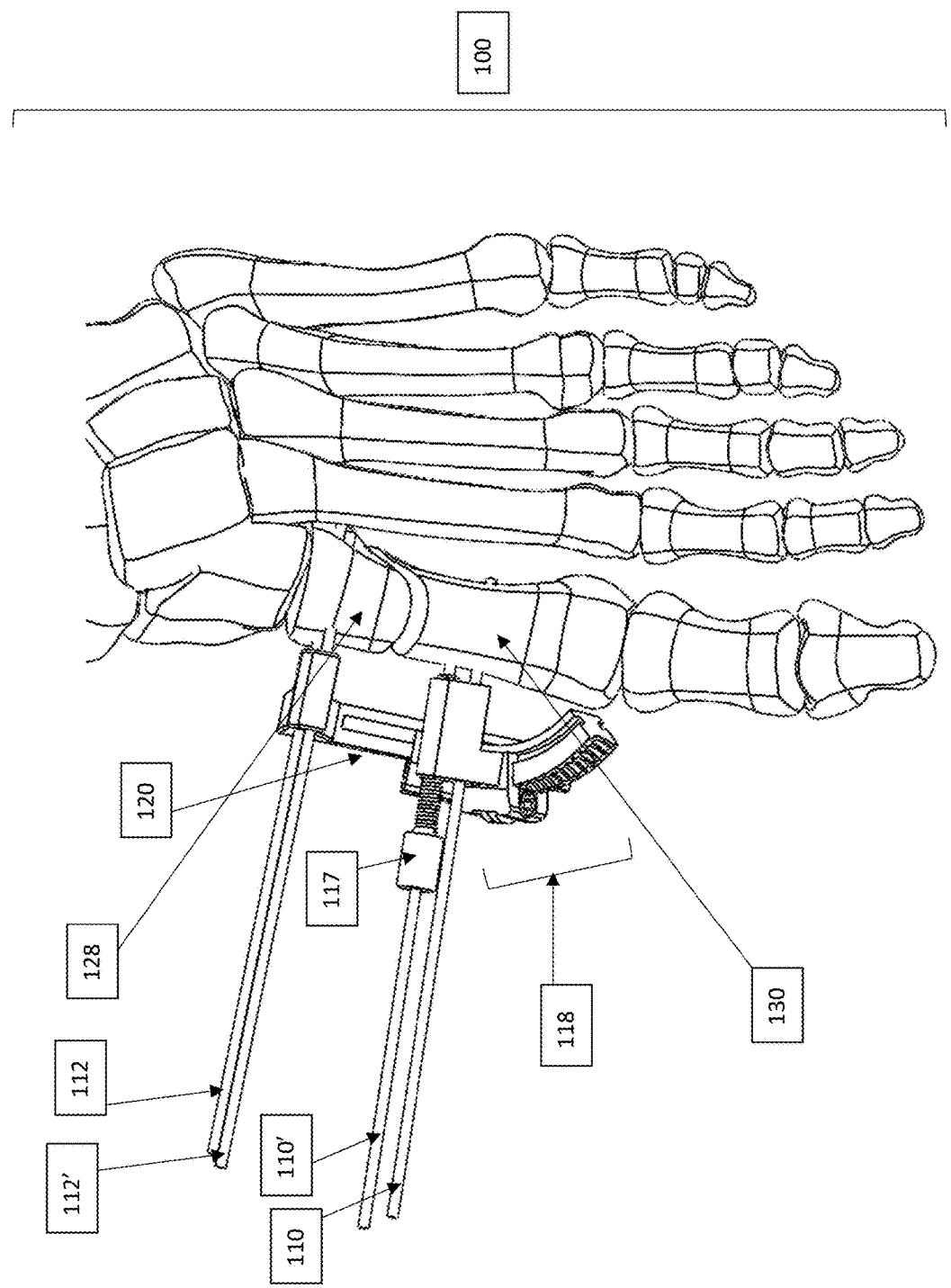
FIG. 7 a top view of the frame and wires of FIG. 6 of the system described herein.

As shown in FIG. 6, for example, first trolley 30 in rotation mechanism 118 may include a mobile or holding portion 35 holding a worm screw 37 received within a recess 39 and movably engaged with teeth 52 to move along an axis of a threaded rail 44. Second trolley 31 in compression-distraction mechanism 120 may include a mobile or holding portion 36, respectively, holding a worm screw 38, respectively, received within a recess 39 and movably engaged with teeth 50, respectively, to move along an axis of a threaded rail 42.

FIG. 6 further depicts a connecting portion 46 that may connect rotation mechanism 118 with compression-distraction mechanism 120. Compression-distraction mechanism 120 may include mobile portion 36. Mobile portion 36 may be movable along a longitudinal axis of compression-distraction mechanism 120. Worm screw 38 may move mobile portion 36 relative to compression-distraction mechanism 120, as described below, thereby moving second trolley 31 relative to the length of compression-distraction mechanism 120. Compression-distraction mechanism 120 and threaded rail 42 may have longitudinal axes aligned parallel to each other, or approximately or about parallel. Compression-distraction mechanism 120 and rotation mechanism 118 of frame 116 may be connected via a connection member 46.

Figure 3:
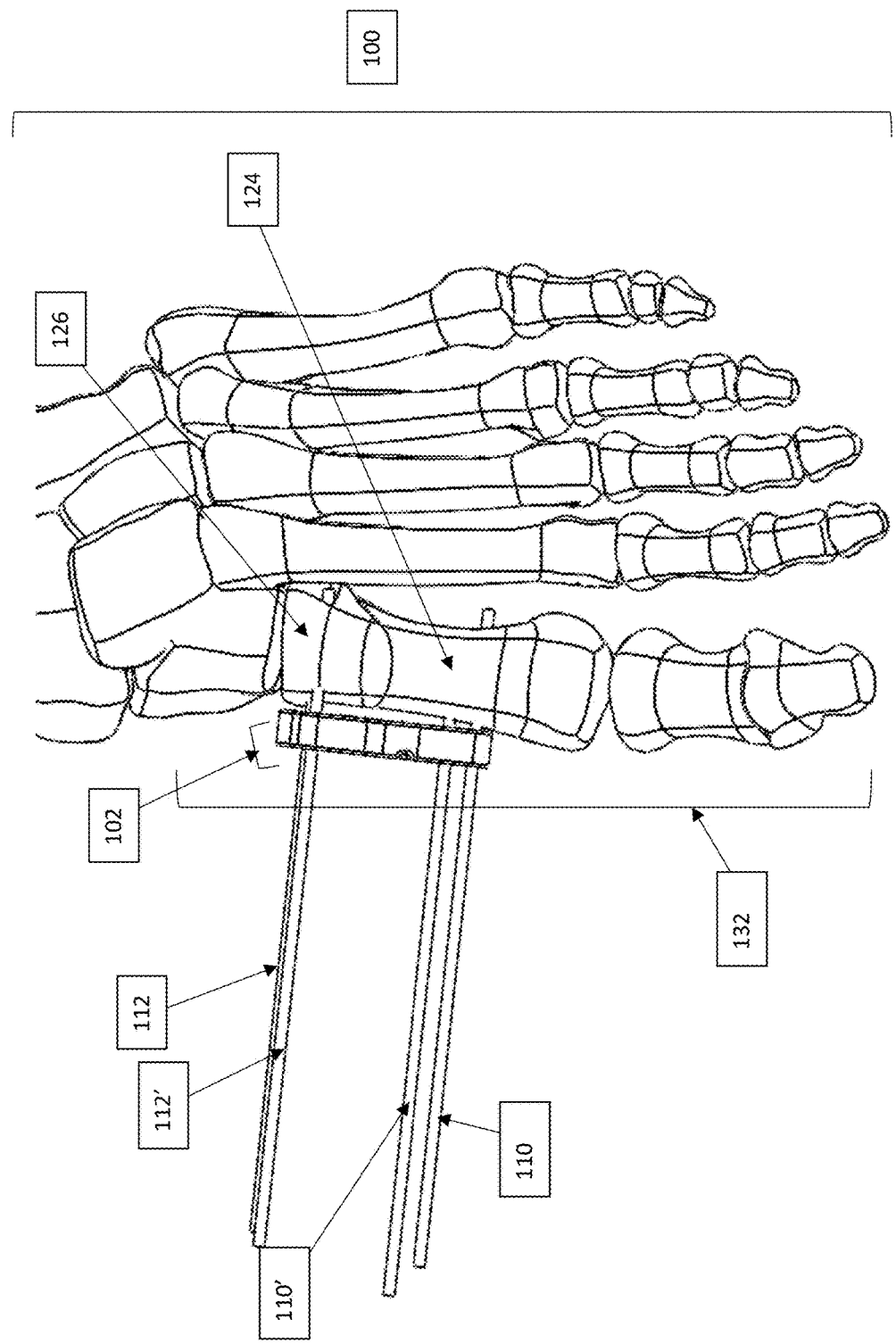
FIG. 3 is a top view of the removable guide of FIG. 2 of the system described herein.
Figure 4:
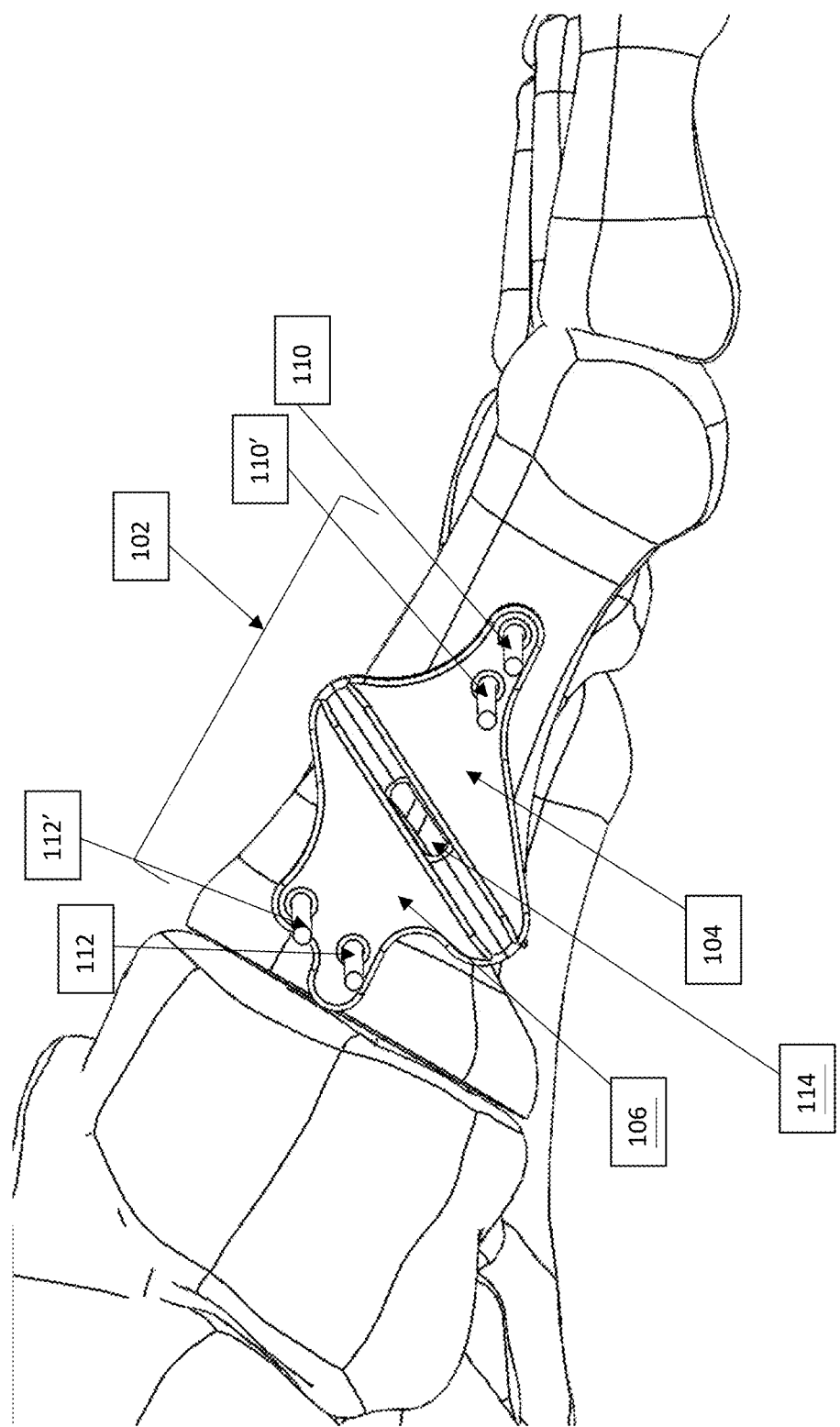
FIG. 4 is a perspective view of a removable guide and wires in accordance with the system described herein, where an osteotomy is performed through the guide.
Figure 13:
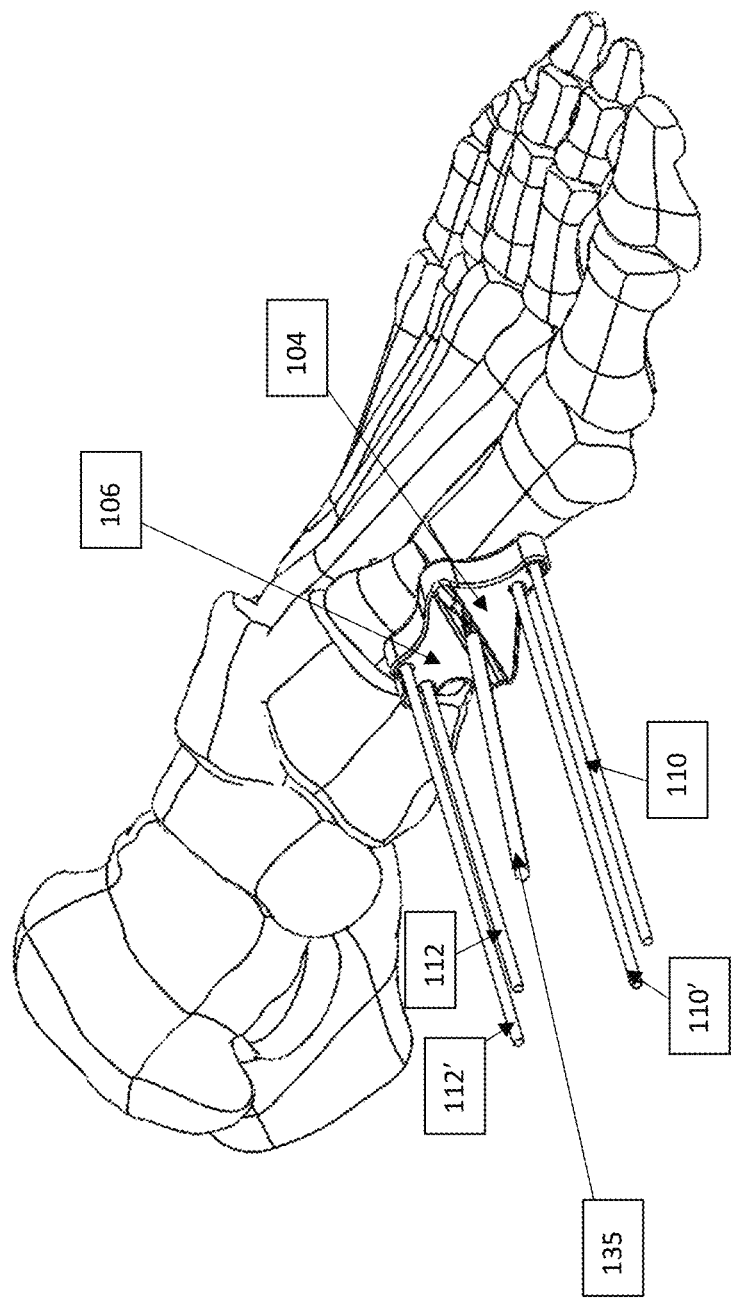
FIG. 13 is a perspective view of the system described herein when a saw is present for an osteotomy procedure.
Figure 14:
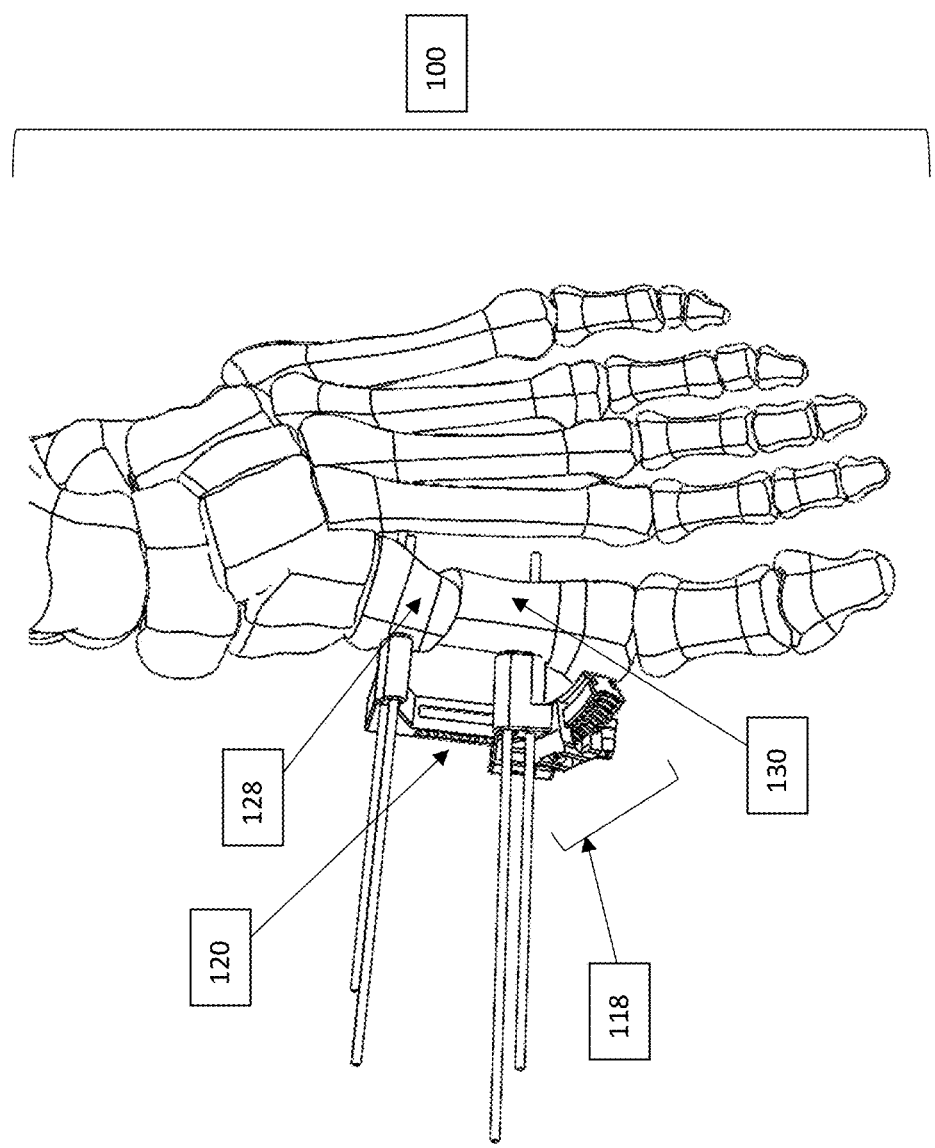
FIG. 14 is a top view of the frame and wires described herein aligning the distal metatarsal fragment.
Figure 15:
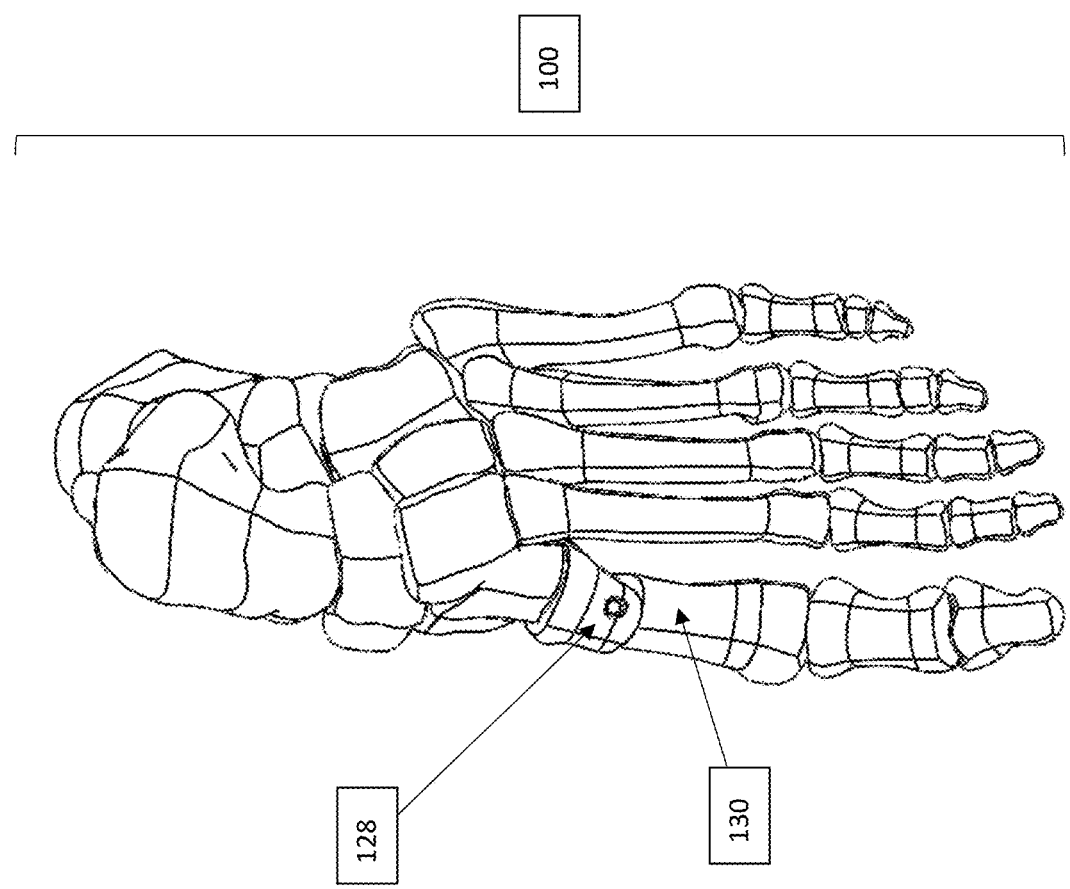
FIG. 15 is a top view of a bunion reduced and fixated with a screw in accordance with the system, devices, and methods described herein.

As depicted in FIGS. 2-5, system 10 may be engaged with a foot 100 by placement of removable guide 102 being received adjacent to the medial side of a first metatarsal 132 (see FIG. 3). As shown in FIG. 3, distal anchoring portion 104 is positioned at a distal end (e.g., distal bone 124) of a first metatarsal (e.g., first metatarsal 132) and where proximal anchoring portion 106 is positioned at a proximal end (e.g., proximal bone 126) of the first metatarsal (e.g., first metatarsal 132). Positioning of removable guide 102 provides alignment of system 10 relative to foot 100. A threaded pin or K-wire referred to as a second wire (110, 110') may be inserted through one or more proximal anchoring aperture (108", 108') into the proximal end of first metatarsal (e.g., proximal bone) 124 of foot 100. An additional set of threaded pin or K-wire referred to as a first wire (112, 112') may be inserted through one or more distal anchoring aperture (108, 108') into the distal end of first metatarsal (e.g., distal bone) 124 of foot 100. Apertures (108, 108', 108", and/or 108''') may have axes which are diverging such that top ends of second set of k-wires (110, 110') and the first set of k-wire (112, 112') may be closer to one another than bottom ends thereof when the k-wires extend through apertures (108, 108', 108", 108') and into a medial side of first metatarsal 132 (see, e.g., FIGS. 3 and 4). An osteotomy is performed through slot 114 (see, e.g., FIG. 13).

During an osteomy performed on first metatarsal 132 through slot 114, proximal bone 126 may be cut and, after cut, is referred to herein as a proximal metatarsal fragment 128. Similarly, during an osteomy performed on first metatarsal 132 through slot 114, distal bone 124 may be cut and, after cut, is referred to herein as a distal metatarsal fragment 130.

Figure 5:
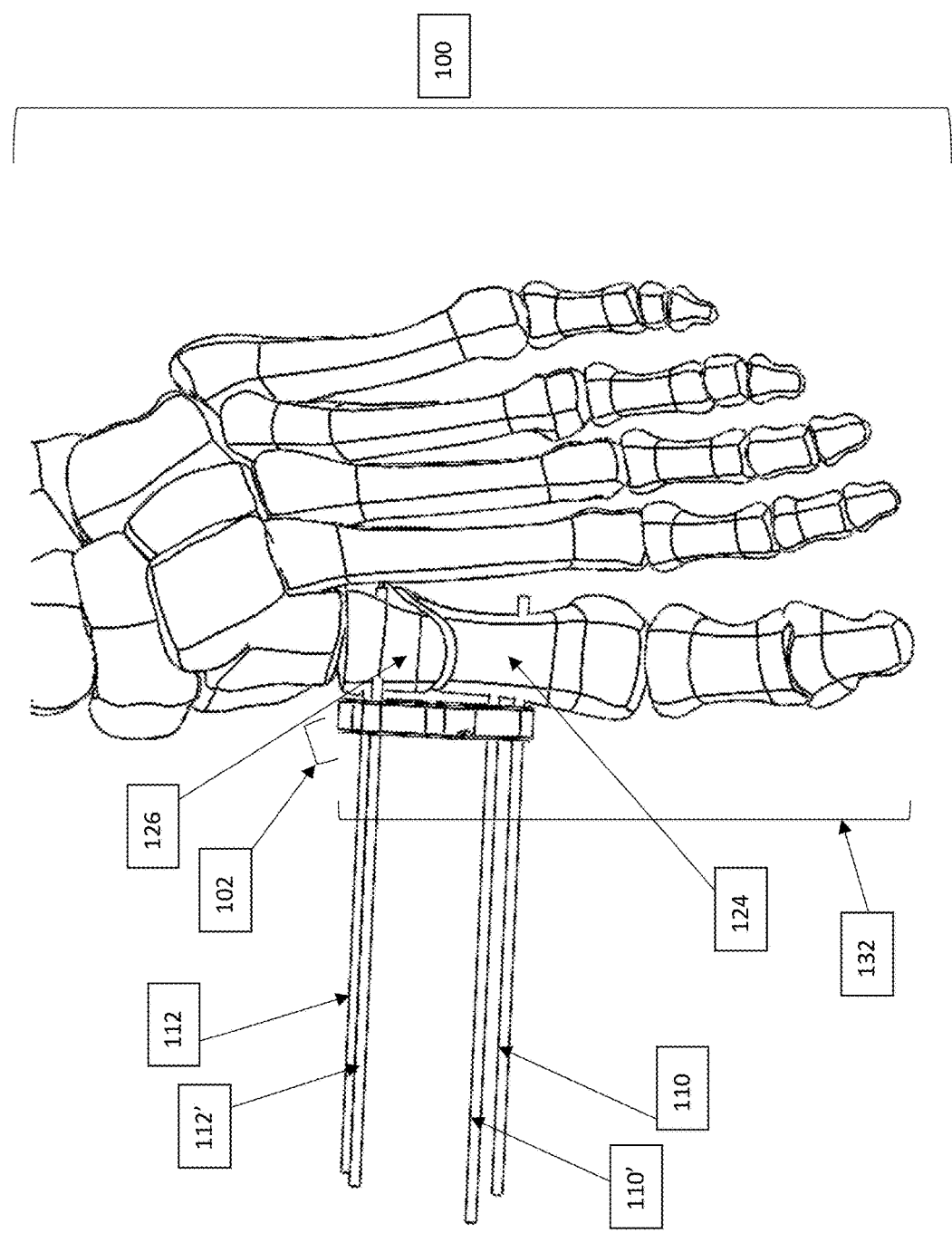
FIG. 5 is a top view of the removable guide and wires of FIG. 4 of the system described herein.

As depicted in FIG. 6 relative to FIG. 5, guide 102 may then be removed from K-wires 110, 110', 112, and 112'. Frame 116 which includes rotation mechanism 118 and compression-distraction mechanism 120 is placed on the medial side of foot 100 so that K-wires 110, 110', 112, and/or 112' are inserted into one or more proximal aperture 122 in compression-distraction mechanism 120 and one or more distal aperture 123 in the rotation mechanism 118.

A valgus angle of first metatarsal (e.g., a valgus angle of distal bone 124 versus proximal bone 126 of first metatarsal 132) may be reduced by hand (e.g., by a surgeon) as shown comparing FIGS. 7, 14, and 15 to FIGS. 8-12. Such movement of first metatarsal (e.g., a valgus angle of distal bone 124 versus proximal bone 126 of first metatarsal 132) may be achieved laterally, rotationally, or a combination of laterally and rotationally. Rotation mechanism 118 contains first trolley 30, which includes mobile or holding portion 35 and worm screw 37, and which moves along a longitudinal axis of rotation mechanism 118 and is capable of moving first metatarsal 132 rotationally. Rotation mechanism 118 includes a curved rail (e.g., threaded rail 44) having mobile portion 35 movably engaged with curved rail (e.g., threaded rail 44) and connected to distal aperture 123 to allow mobile portion 35 to move rotationally relative to an axis that is perpendicular to an arc formed by the rotational movement when compression-distraction mechanism 120 is engaged with proximal bone 126 and distal aperture 123 receives second wire or wires (110 and/or 110') to connect rotation mechanism 118 to distal bone 124. Threaded rail 44 includes a longitudinal arc having a center on an axis of an arc of an osteotomy performed using slot 114 of guide 102 when guide 102 is received on wires 110, 110', 112, and 112' as described above. For example, the longitudinal arc of threaded rail 44 when received on wires 110, 110', 112, and 112' may be parallel to a longitudinal curved dimension of slot 114 when guide 102 is received on wires 110, 110', 112, and 112'. Rotation mechanism 118 may be connected to distal bone 124 by second wire 110 and/or 110' received in distal aperture 123. Curved rail 44 in rotation mechanism 118 may include screw 37 engaging curved rail 44 and mobile portion 35 to allow movement of mobile portion 35 and distal bone 124 relative to proximal bone 126 when a user drives screw 37. Curved rail 44 in rotation mechanism 118 includes a curved rail longitudinal axis along threaded rail 44.

Figure 8:
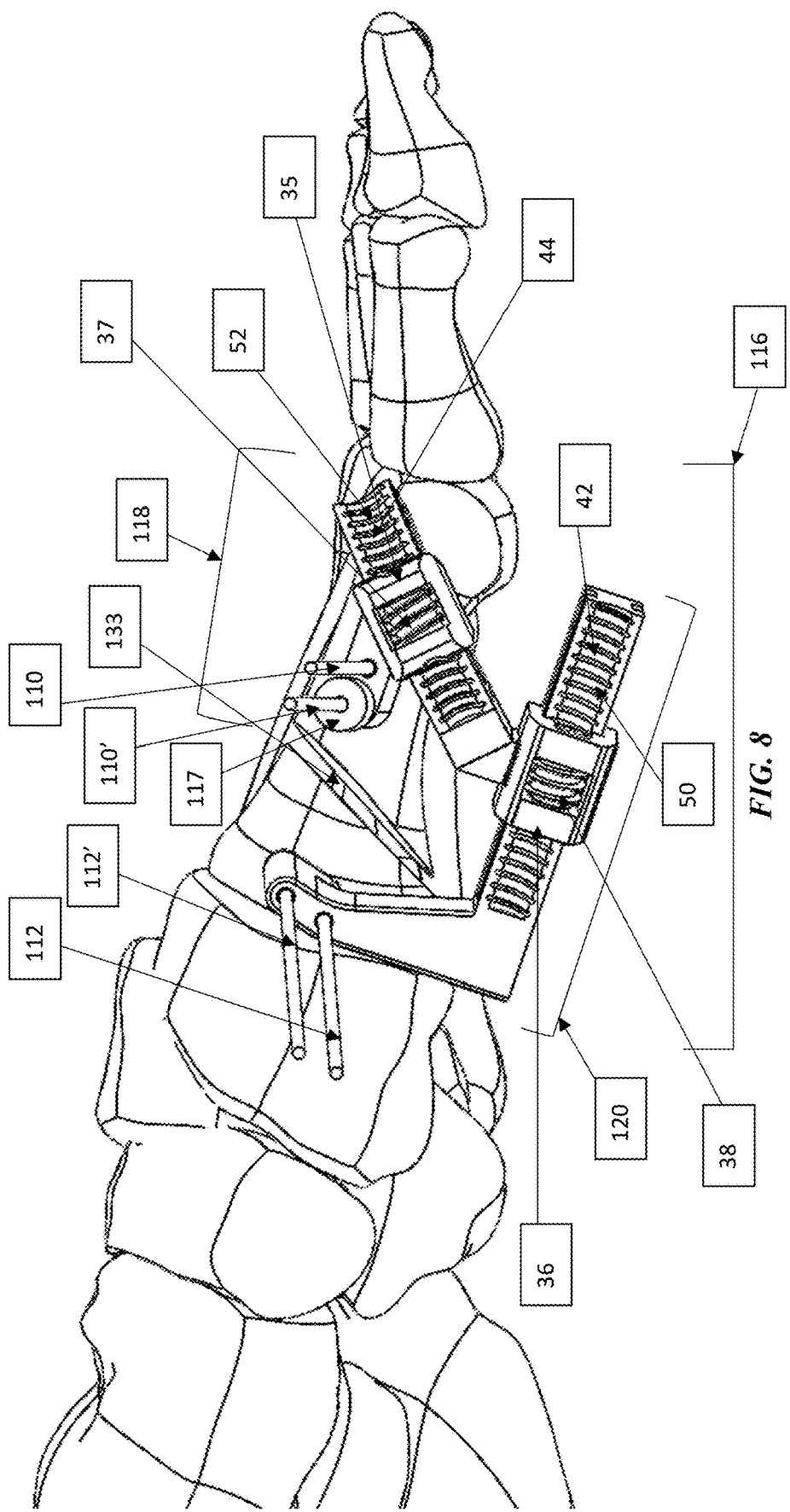
FIG. 8 is a perspective view of the frame and wires in accordance with the system described herein, where the first distal metatarsal fragment is rotated using a curved rail correcting frontal plane rotation and intermetatarsal angle.
Figure 9:
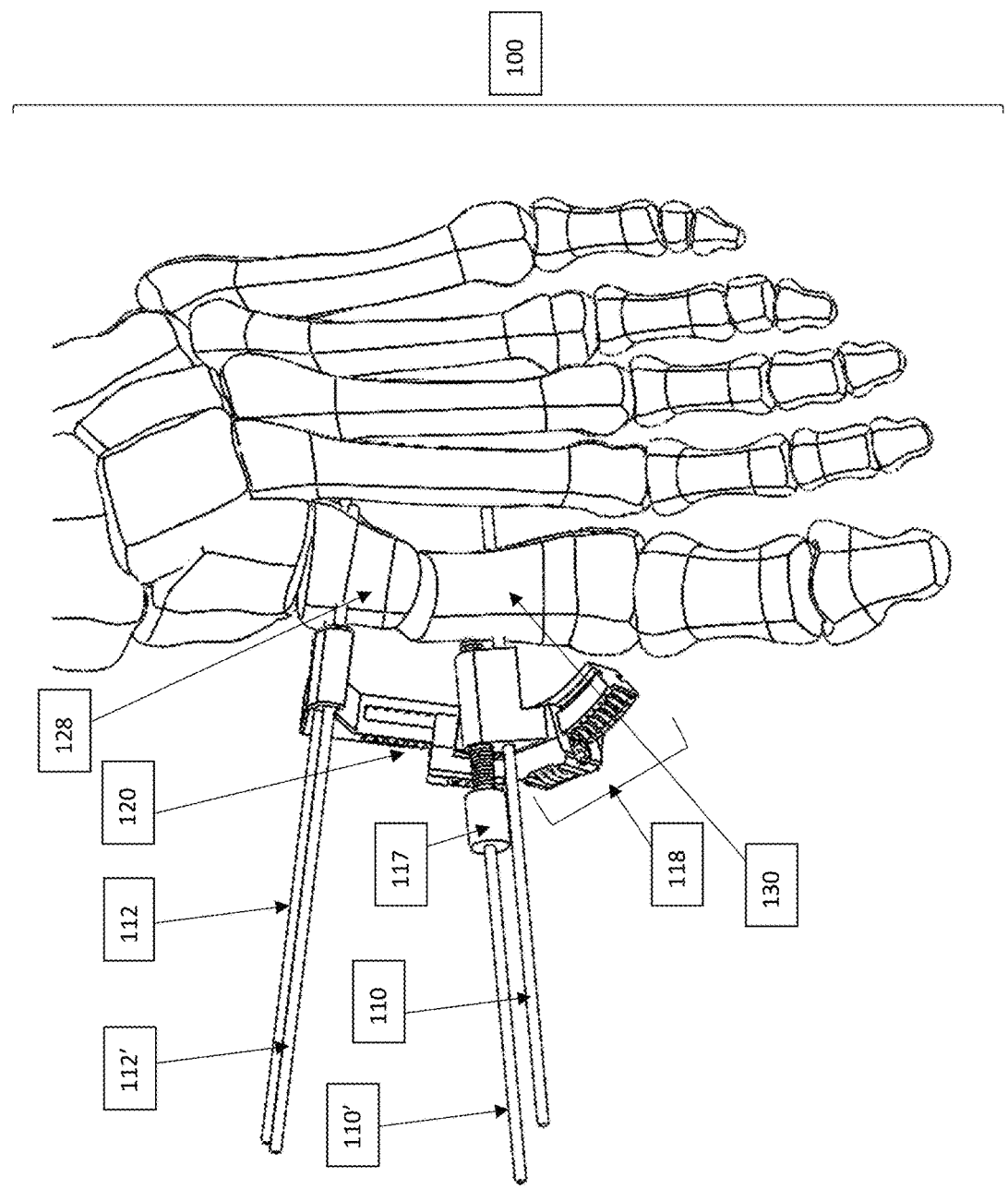
FIG. 9 is a top view of the frame and wire of FIG. 8 of the system described herein.
Figure 10:
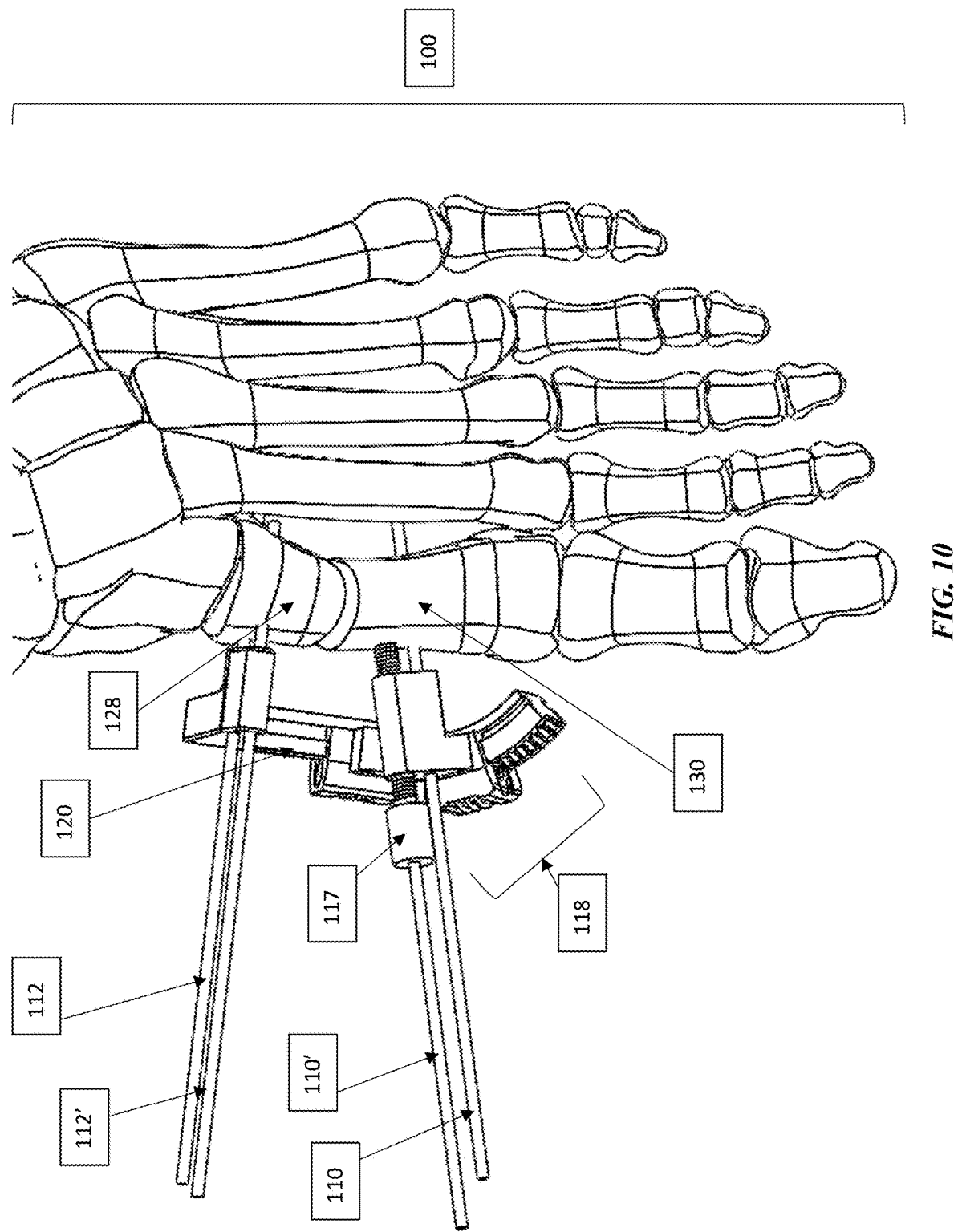
FIG. 10 is a top view of the system described herein where the lateral positioning mechanism is used to push the first distal metatarsal fragment laterally.
Figure 11:
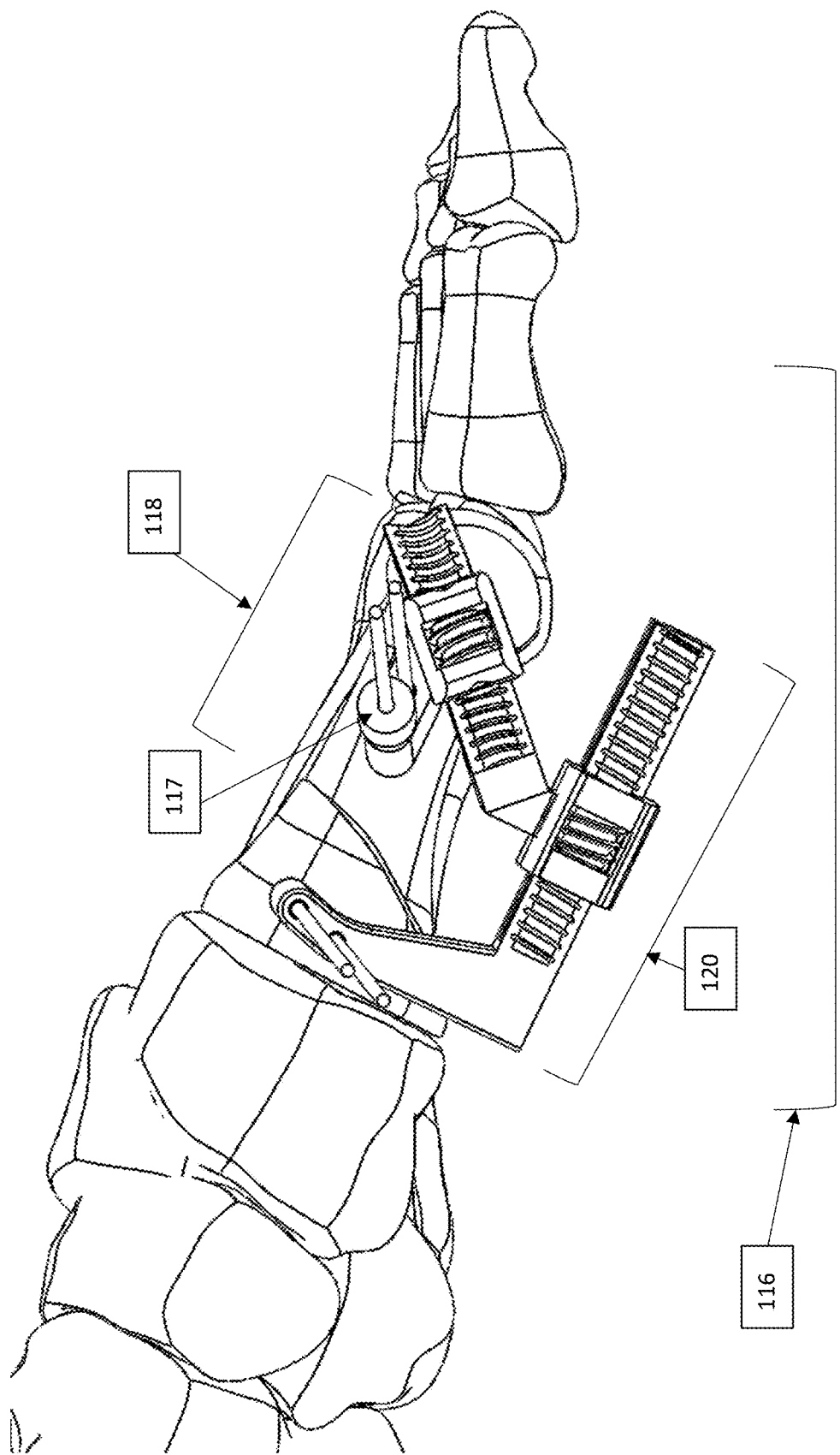
FIG. 11 is perspective view of the frame and wires of the system described herein, wherein the first distal metatarsal fragment is compressed to the proximal metatarsal fragment using a linear rail.
Figure 12:
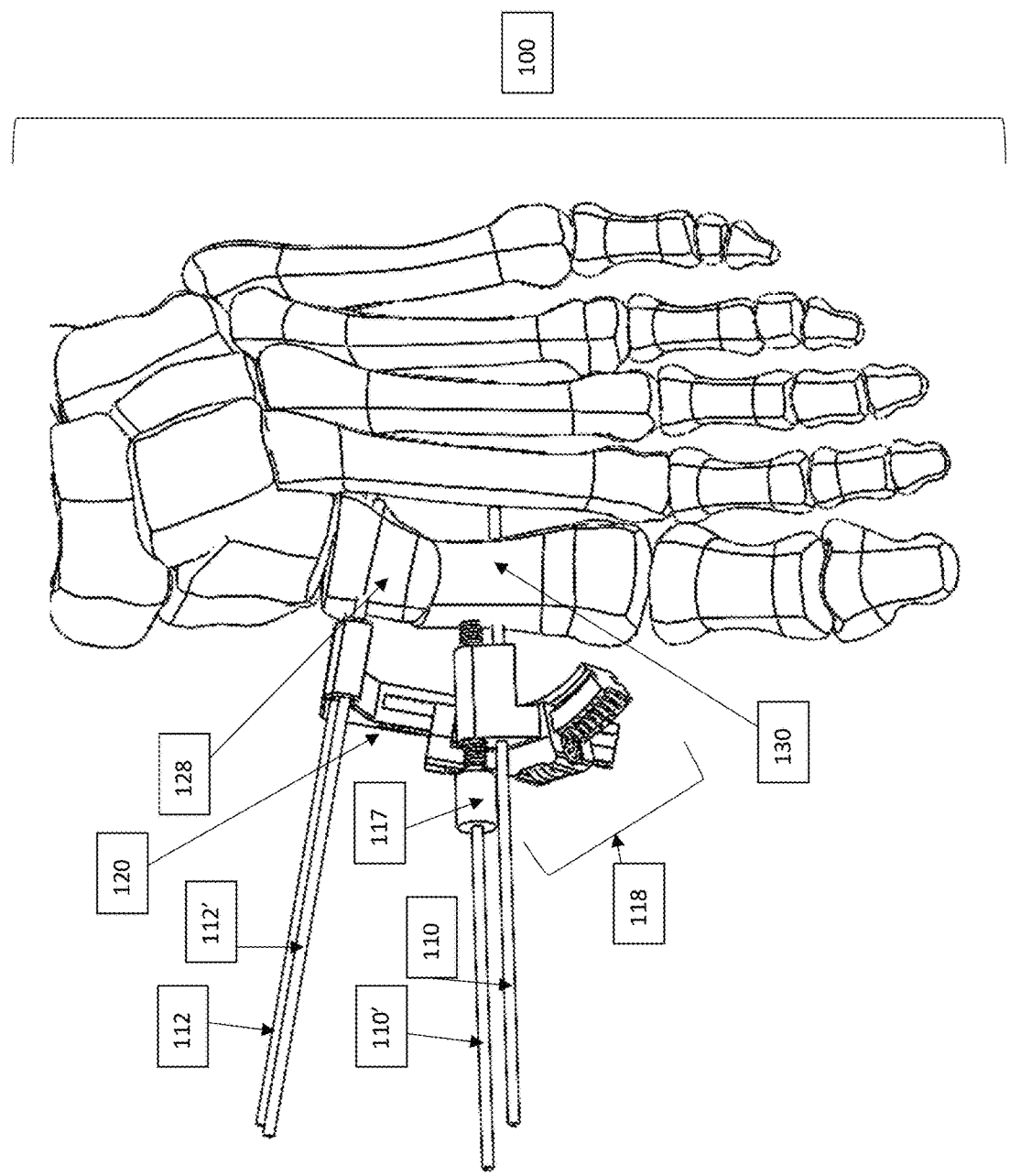
FIG. 12 is a top view of the frame and wires of the system described herein and as shown in FIG. 11.

As depicted in, for example, FIGS. 6 and 8, compression-distraction mechanism 120 includes a linear rail longitudinal axis (e.g., a linear threaded rail 42). Compression-distraction mechanism 120 includes linear rail (e.g., a threaded rail 42) that has mobile portion 36 movably engaged with linear rail 42 to allow mobile portion 36 to move laterally relative to a longitudinal axis of compression-distraction mechanism 120. Compression-distraction mechanism 120 may include a proximal aperture 122 for receiving one or more first wires (112 and/or 112') to connect compression-distraction mechanism 120 to proximal bone 126. Compression-distraction mechanism 120 is connected to proximal bone 126 by proximal aperture 122 and one or more first wires (112 and/or 112'). Frame 116 is connectable to proximal bone 126 by one or more first wire (112 and/or 112') received in proximal aperture 122. Linear rail 42 allows a clinician to distract and compress the distal metatarsal fragment 130.

Proximal anchoring portion 106 of guide 102 may include second proximal anchoring aperture (interchangeably referred to herein as 108" and/or 108''') to receive a third wire (interchangeably referred to herein as any wire in addition to the first wire 112 and/or 112'). Distal anchoring portion 104 of guide 102 may include second distal anchoring aperture (interchangeably referred to herein as 108 and/or 108') to receive a fourth wire (interchangeably referred to herein as any wire in addition to the second wire 110 and/or 110').

As depicted in FIGS. 9-12, holding portion 35 and/or 36 may be moved (e.g., via a manipulation or rotation of worm screw 37 and/or 38, respectively, by a user) along rail 42 and/or 44 upon which is first trolley 30 and/or second trolley 31, respectively, until a longitudinal dimension of one or more first wire 112 and/or 112' or one or more second wire 110 and/or 110' is perpendicular or about perpendicular to longitudinal dimensions of sesamoids of first metatarsal 132. Such movement of holding portion 35 and/or 36 connected to first metatarsal 132 by one or more first wire 112 and/or 112' or one or more second wire 110 and/or 110' may further adjust the valgus angle of first metatarsal 132.

Removable guide 102 includes slot 114 which may be utilized for an open procedure while a Bur guide (not shown) may be used for a MIS (Minimally Invasive Surgery) procedure. Such an open procedure could involve an incision (e.g., of 4-5 cm) separating a proximal bone fragment 128 of first metatarsal 132 and a distal bone fragment 130 of first metatarsal 132, for example, while an MIS procedure would involve incisions only at the locations necessary for the insertion of particular instruments. For example, a Bur guide cartridge (not shown) may include a 2.3 mm Shannon Burr usable to bur a joint space.

As depicted in FIGS. 1-4, guide 102 may include slot 114 of any suitable size or dimension. For example, slot 114 may be about 1.5 mm, about 3 mm, less than about 1.5 mm, more than about 3 mm, or any amount between about 1.0 mm and about 4 mm. Guide 102 and slot 114 is placed on a medial side of first metatarsal 132 and assists a clinician in making the desired osteotomy.

As depicted in FIGS. 6-12, a driver may be engaged with mobile portion 36 of compression-distraction mechanism 120 to rotate worm screw 38 received in an interior cavity of mobile portion 36. Worm screw 38 may engage an interior threaded surface (not shown) of mobile portion 36 bounding cavity 39 and a top threaded surface of compression-distraction mechanism 120. A rotation of the driver and worm screw 38 clockwise or counter-clockwise may cause movement of mobile portion 36 along the length of compression-distraction mechanism 120 due to engagement of worm gear with threaded surface or rail 42 and interior threaded surface of mobile portion 36 to cause a movement of second trolley 31 connected to the proximal bone to move such a bone laterally, as depicted.

As further depicted in FIG. 6-12, a driver may be engaged with mobile portion 35 of rotation mechanism 118 to rotate worm screw 37 received in an interior cavity of mobile portion 35. Worm screw 37 may engage an interior threaded surface (not shown) of mobile portion 35 bounding cavity and top threaded surface 44 of rotation mechanism 118. A rotation of driver and worm screw 37 counter clockwise or counter-clockwise may cause movement of mobile portion 35 along the length of rotation mechanism 118 due to engagement of worm gear with threaded surface 44 and interior threaded surface of mobile portion 35 to cause a movement of first trolley 30 connected to distal bone 124 (or distal metatarsal fragment 130) to move such a bone rotationally, as depicted.

Frame 116 which includes rotation mechanism 118 and compression-distraction mechanism 120 allows for controlled means of manipulating a distal metatarsal fragment (e.g., distal bone fragment 130) in both rotation and lateral translation. Frame 116 includes curved rail 44 in rotation mechanism 118 such that the curve is in a plane parallel to the osteotomy performed, for example between the proximal metatarsal fragment 128 (of, for example, proximal bone 126) of the first metatarsal 132 and the distal metatarsal fragment 130 (of, for example, distal bone 124) of the first metatarsal 132. Curved rail 44 enables the clinician to rotate distal metatarsal fragment 130 of the first metatarsal 132. This rotation corrects both frontal plane deformity and intermetatarsal angle. Compression-distraction mechanism 120 is capable of distracting (i.e., moving apart) bone fragments (e.g., distal metatarsal fragment 130 and/or proximal metatarsal fragment 128) and compressing those fragments back together. For example, FIGS. 6 and 8 depict distal metatarsal fragment 130 and proximal metatarsal fragment 128 after the fragments being cut from one another (e.g., using guide 102) and the fragments being distracted to provide a space 133. Rotation by rotation mechanism 118 may be undertaken while distracted partially, distracted fully, or not distracted at all.

After the one or more bones, for example, proximal end of first metatarsal (e.g., proximal bone 126) and distal end of first metatarsal (e.g., distal bone 124) have been cut as described above (e.g., using guide 102 and a saw) or otherwise prepared, the driver may be engaged with a worm gear as described above and rotated clockwise or counter-clockwise, for example, to move mobile portion 35 along or rotation mechanism 118 and/or move mobile portion 36 along compression-distraction mechanism 120, to move respective first trolley 30 and/or second trolley 31 to thereby move one or more bone fragments, for example a distal metatarsal bone fragment 130) or a proximal metatarsal bone fragment 128) as depicted in FIGS. 9-12. A plate, such as a medial Lapidus plate, may optionally be attached to the bone (e.g., first metatarsal at either the proximal fragment or the distal fragment) to connect the bones.

As depicted in FIGS. 9-12, system 10 as described above may further include a lateral positioning mechanism 117. Lateral positioning mechanism 117 may be positioned on one or more second wire (110 and/or 110') and adjacent to frame 116 to allow lateral movement of proximal bone 126 (or proximal metatarsal fragment 128). Lateral positioning mechanism 117 may include a bolt and a threaded post connected to distal anchoring portion 104, where one or more second wire (110 and/or 110') is positioned through a center of threads of the threaded post. Lateral positioning mechanism 117 may include an alignment slot (e.g., aligned, shaped and dimensioned) to direct a screw or bolt therethrough into a desired location to connect two bones (e.g., proximal bone 126 and distal bone 124) together while avoiding a K-wire already present in the bone as depicted in FIGS. 1-12. A second screw guide may be present. Lateral positioning mechanism 117 (e.g., push bolt) allows a clinician to translate distal bone (e.g., distal metatarsal fragment 130) laterally to further reduce the prominence of the metatarsal head on the medial side of foot 100.

In an undepicted example, K-wires can be placed free handed to keep a first metatarsal (e.g., first metatarsal 132) in place while removing system 10 and an interosseous system may be inserted such as that described in U.S. Pat. No. 10,987,146 incorporated herein by reference.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:
1. A bone displacement system comprising:
a removable guide comprising a proximal anchoring portion and a distal anchoring portion, the proximal anchoring portion having a proximal anchoring aperture for receiving a first wire to connect the guide to a proximal bone, and the distal anchoring portion having a distal anchoring aperture for receiving a second wire to connect the guide to a distal bone, wherein the guide further comprises a slot configured to receive a tool; and
a frame comprising a compression-distraction mechanism and a rotation mechanism, wherein said compression-distraction mechanism is connected to said rotation mechanism and engageable with the proximal bone, said rotation mechanism comprising a distal aperture for receiving the second wire to connect the rotation mechanism to the distal bone, wherein the compression-distraction mechanism is configured to move the rotation mechanism and the distal bone relative to the proximal bone;
wherein said rotation mechanism comprises a curved rail having a mobile portion movably engaged with the curved rail; and
wherein said curved rail comprises a rail longitudinal arc having an axis having an orientation when the frame is connected to the distal bone that is parallel to an orientation of said slot when said removable guide is connected to the proximal bone and the distal bone.

2. The system of claim 1, wherein said rotation mechanism is configured to be connected to the distal bone by the second wire received in the distal aperture.

3. The system of claim 1, wherein said curved rail comprises a screw engaging the curved rail and the mobile portion to allow movement of the mobile portion and the distal bone relative to the proximal bone when a user drives said screw.

4. The system of claim 1, wherein the curved rail comprises a curved rail longitudinal arc, and the compression-distraction mechanism comprises a longitudinal axis.

5. The system of claim 1, wherein said compression-distraction mechanism comprises a linear rail having a mobile portion movably engaged with said linear rail to allow said mobile portion to move.

6. The system of claim 1, wherein the compression-distraction mechanism comprises a proximal aperture for receiving the first wire to connect the compression-distraction mechanism to the proximal bone.

7. The system of claim 6, wherein said frame is connectable to the proximal bone by the first wire received in the proximal aperture.

8. The system of claim 1, wherein said compression-distraction mechanism and said rotation mechanism of said frame are connected via a connection member.

9. The system of claim 1, wherein the proximal anchoring portion of the guide comprises a second proximal anchoring aperture to receive a third wire.

10. The system of claim 1, wherein the distal anchoring portion of the guide comprises a second distal anchoring aperture to receive a fourth wire.

11. The system of claim 1 further comprising:
a lateral positioning mechanism.

12. The system of claim 11, wherein said lateral positioning mechanism is configured to be positioned on said second wire.

13. The system of claim 11, wherein said lateral positioning mechanism comprises a threaded post connected to said distal anchoring portion, wherein said second wire is configured to be positioned through a center of said post.

14. A mechanism for bone displacement comprising:
a removable guide comprising a slot;
a frame comprising a compression-distraction mechanism and a rotation mechanism, wherein said compression-distraction mechanism is connected to said rotation mechanism and engageable with a proximal bone, said rotation mechanism comprising a distal aperture for receiving a wire to connect the rotation mechanism to a distal bone, wherein the compression-distraction mechanism is configured to move the rotation mechanism and to move the proximal bone and distal bone relative to each other;
wherein said rotation mechanism comprises a curved rail having a mobile portion movably engaged with the curved rail; and
wherein said curved rail comprises a rail longitudinal arc having an axis having an orientation when the frame is connected to the distal bone that is parallel to an orientation of said slot when the guide is connected to the proximal bone and the distal bone.

15. The mechanism of claim 14, wherein said curved rail comprises a screw engaging the curved rail and the mobile portion to allow movement of the mobile portion and the distal bone relative to the proximal bone when a user drives said screw.

16. The mechanism of claim 14, wherein the compression-distraction mechanism comprises a proximal aperture for receiving a first wire to connect the compression-distraction mechanism to the proximal bone.

17. The mechanism of claim 14, wherein the curved rail has a curved rail longitudinal arc, and the compression-distraction mechanism has a longitudinal axis.

18. The mechanism of claim 14, wherein said compression-distraction mechanism comprises a linear rail having a mobile portion movably engaged with said linear rail to allow said mobile portion to move.

19. The mechanism of claim 14, wherein said compression-distraction mechanism and said rotation mechanism of said frame are connected via a connection member.

20. The mechanism of claim 14, wherein the compression-distraction mechanism comprises a proximal aperture to receive a wire.

21. The mechanism of claim 14, wherein the rotation mechanism comprises a second distal aperture to receive a wire.

22. The mechanism of claim 14 further comprising:
a lateral positioning mechanism.

23. The mechanism of claim 22, wherein said lateral positioning mechanism is configured to be positioned on said second wire.

24. The mechanism of claim 22, wherein said lateral positioning mechanism comprises a threaded post connected to said distal anchoring portion.

* * * * *